US010813545B2

(12) United States Patent
MacLean et al.

(10) Patent No.: US 10,813,545 B2
(45) Date of Patent: Oct. 27, 2020

(54) MEDICAL ILLUMINATION DEVICE AND RELATED METHODS

(71) Applicant: Boston Scientific Scimed, Inc., Maple Grove, MN (US)

(72) Inventors: Brian MacLean, Cary, NC (US); Edward Sinofsky, Dennis, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 70 days.

(21) Appl. No.: 16/054,553

(22) Filed: Aug. 3, 2018

(65) Prior Publication Data

US 2019/0038120 A1 Feb. 7, 2019

Related U.S. Application Data

(60) Provisional application No. 62/541,428, filed on Aug. 4, 2017.

(51) Int. Cl.
*A61B 1/07* (2006.01)
*A61B 1/00* (2006.01)
*A61B 1/06* (2006.01)
*A61B 18/22* (2006.01)
*F21V 8/00* (2006.01)
*G02B 6/04* (2006.01)
*G02B 6/42* (2006.01)

(52) U.S. Cl.
CPC ............ *A61B 1/07* (2013.01); *A61B 1/00117* (2013.01); *A61B 1/00126* (2013.01); *A61B 1/0638* (2013.01); *A61B 1/0653* (2013.01); *A61B 1/0684* (2013.01); *A61B 18/22* (2013.01); *A61B 1/00105* (2013.01); *G02B 6/0006* (2013.01); *G02B 6/04* (2013.01); *G02B 6/4298* (2013.01)

(58) Field of Classification Search
CPC ... A61B 1/07; A61B 1/00117; A61B 1/00126; A61B 1/0638; A61B 1/0653; A61B 1/0684; A61B 1/00105; A61B 18/22; G02B 6/04; G02B 6/4298; F21V 33/0068; Y10S 362/804
USPC .................. 600/199, 249; 362/553, 572–575
See application file for complete search history.

(56) References Cited

U.S. PATENT DOCUMENTS

| | | | |
|---|---|---|---|
| 7,798,692 B2 | 9/2010 | Krupa et al. | |
| 2008/0221388 A1* | 9/2008 | Seibel | A61B 1/0008 600/109 |
| 2009/0040754 A1* | 2/2009 | Brukilacchio | A61B 1/0653 362/228 |

(Continued)

OTHER PUBLICATIONS

International Search Report and Written Opinion of International Searching Authority, dated Nov. 7, 2018, 15 pages.

*Primary Examiner* — Eduardo C Robert
*Assistant Examiner* — David C Comstock
(74) *Attorney, Agent, or Firm* — Bookoff McAndrews, PLLC

(57) ABSTRACT

An illumination device may include an illumination source including a light source, a single fiber connecting the illumination source to a medical device and being dedicated to the transmission of light energy from the light source, and a numerical aperture adjustment portion located between the single fiber and the medical device. The light source may generate at least one non-white colored laser energy, and the illumination device may convert the at least one non-white colored laser energy into white colored laser energy.

20 Claims, 3 Drawing Sheets

(56) References Cited

U.S. PATENT DOCUMENTS

| | | |
|---|---|---|
| 2010/0010314 A1 | 1/2010 | Krattiger et al. |
| 2014/0107413 A1 | 4/2014 | Tremaglio et al. |
| 2014/0198480 A1 | 7/2014 | Dai et al. |
| 2015/0374218 A1 | 12/2015 | Nishio et al. |
| 2016/0106299 A1 | 4/2016 | Kamee et al. |
| 2017/0209032 A1* | 7/2017 | Matsunobu .......... G02B 6/0008 |

* cited by examiner

MEDICAL ILLUMINATION DEVICE AND RELATED METHODS

CROSS-REFERENCE TO RELATED APPLICATIONS

This patent application claims the benefit of priority under 35 U.S.C. § 119 to U.S. Provisional Patent Application No. 62/541,428, filed Aug. 4, 2017, which is herein incorporated by reference in its entirety.

TECHNICAL FIELD

Various aspects of the present disclosure relate generally to systems, devices, and methods useful in medical procedures. More specifically, the present disclosure relates to systems, devices, and methods for illuminating medical procedures.

BACKGROUND

Internal medical procedures often require an illumination source to allow the medical professional to visualize the surgical site. Light emitting diode ("LED") sources are commonly used to provide the illumination source. LED sources positioned near the surgical site often generate detrimental heat. LED sources often emit light at insufficient luminosity or low angles as well. LED sources may deliver illumination through an insertion device, for example, an endoscope, to the surgical site. However, these LED sources often consume considerable power and require large and/or heavy cables of fiber bundles with metal jackets to connect the LED source to the insertion device. Such cables and their connection to the insertion device may encumber the ergonomic use of the insertion device, as the connection interferes with and/or restricts the manipulation of the insertion device handle. The LED sources themselves are often large and cumbersome, further interfering with the medical procedure.

The systems, devices, and methods of the current disclosure may rectify some of the deficiencies described above, and/or address other aspects of the prior art.

SUMMARY

Examples of the present disclosure relate to, among other things, medical systems, devices, and methods. Each of the examples disclosed herein may include one or more of the features described in connection with any of the other disclosed examples.

In one example, an illumination device may comprise an illumination source including a light source, a single fiber connecting the illumination source to a medical device and being dedicated to the transmission of light energy from the light source, and a numerical aperture adjustment portion located between the single fiber and the medical device. The light source may generate at least one non-white colored laser energy, and the illumination device may convert the at least one non-white colored laser energy into white colored laser energy.

The single fiber may be a single filament glass fiber encased in a flexible polymeric jacket. The fiber may have a diameter of approximately 0.4 mm. The light source may be battery powered. The light source may include at least one laser diode to generate a blue color laser. The blue color laser may include a wavelength of approximately 445 to 455 nanometers. The single fiber may include a connector configured to couple the single fiber to the medical device. The connector may include a light guide and a heatsink, and the numerical aperture adjustment portion may be a truncated cone that includes an exit face larger than an entrance face. The light guide may include a sapphire rod, and an end of the sapphire rod may be coated with a fluorescent material. The fluorescent material may include a polymeric material that includes phosphor particles. The silicone material may include both phosphor particles and non-fluorescent scattering particles.

The light source may include at least one red laser diode configured to generate a red color laser, at least one green laser diode configured to generate a green color laser, and at least one blue laser diode configured to generate a blue color laser. The at least one red laser diode, the at least one green laser diode, and the at least one blue laser diode may be each coupled to a light source fiber, and the light source fibers may be coupled to form one source fiber within the illumination source to form white laser energy. The at least one red laser diode, the at least one green laser diode, and the at least one blue laser diode may be each coupled to a light source fiber, and the light source fibers may be coupled to the single fiber to form white laser energy. The single fiber may include a connector configured to couple the single fiber to the medical device, and the numerical aperture adjustment portion may be a beam expansion portion between an end of the single fiber and the medical device.

In another example, an illumination device may comprise an illumination source and an illumination conveying element. The illumination conveying element may include a connector configured to connect the illumination conveying element to a medical device. The connector may include a light guide and a numerical aperture converter. A surface of the light guide may be coated with a fluorescent material, and the fluorescent material may abut the numerical aperture converter.

The illumination source may include at least one laser diode to generate a blue color laser having a wavelength of approximately 445 to 455 nanometers. The numerical aperture converter may be a truncated quartz cone having an entrance face and an exit face, the entrance face having a smaller diameter than the exit face. The fluorescent material may be a silicone based material that includes fluorescent phosphor particles and non-fluorescent scattering particles. The illumination conveying element may be a single filament glass fiber encased in a flexible polymeric jacket. The illumination conveying element may have a diameter of approximately 0.4 mm. The connector may be coupled to the medical device, and at least one illumination lumen within the medical device may direct illumination to a distal end of the medical device.

In a further aspect, an illumination device may comprise an illumination source and a fiber. The illumination source may include at least three light energy sources, each having a different wavelength, and light energy from the light energy sources may combine to form white light either within the fiber or before being transmitted into the fiber.

The laser energy sources may include at least one red laser diode configured to generate a red color laser, at least one green laser diode configured to generate a green color laser, and at least one blue laser diode configured to generate a blue color laser. The at least one red laser diode, the at least one green laser diode, and the at least one blue laser diode may be each coupled to a light source fiber, and the light source fibers may be coupled to form one source fiber within the illumination source to form white laser energy. The at least one red laser diode, the at least one green laser diode, and the at least one blue laser diode may be each coupled to a light source fiber, and the light source fibers may be coupled to the fiber to form white laser energy. The fiber may include a fiber connector connecting the fiber to an illumination port in a medical device, and the fiber connector may include a coupling gap between an end of the fiber and the illumination port. The coupling gap may allow light energy from the fiber to expand approximately 0.2 numerical apertures.

Both the foregoing general description and the following detailed description are exemplary and explanatory only and are not restrictive of the features, as claimed. As used herein, the terms "comprises," "comprising," "having," including," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal." As used herein, the terms "about," "substantially," and "approximately," indicate a range of values within +/−5% of a stated value.

BRIEF DESCRIPTION OF THE FIGURES

The accompanying drawings, which are incorporated in and constitute a part of this specification, illustrate various exemplary embodiments and together with the description, serve to explain the principles of the disclosure.

DETAILED DESCRIPTION

Examples of the present disclosure include systems, devices, and methods to facilitate, and improve the efficacy and safety of illumination during medical procedures. For example, aspects of the present disclosure may provide a user (e.g., a physician, medical technician, or other medical service provider) with the ability to more easily view a patient's interior lumen with clear illumination, without some of the encumbrances of a bulky connection cable or the risk of detrimental heat build-up. In some embodiments, for example, the present disclosure may be used in performing an endoscopic, hysteroscopic, or ureteroscopic procedure.

Reference will now be made in detail to examples of the present disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary medical device or insertion device. When used herein, "proximal" refers to a position relatively closer to the exterior of the body or closer to an operator using the medical device or insertion device. In contrast, "distal" refers to a position relatively farther away from the operator using the medical device or insertion device, or closer to the interior of the body.

Figure 1:
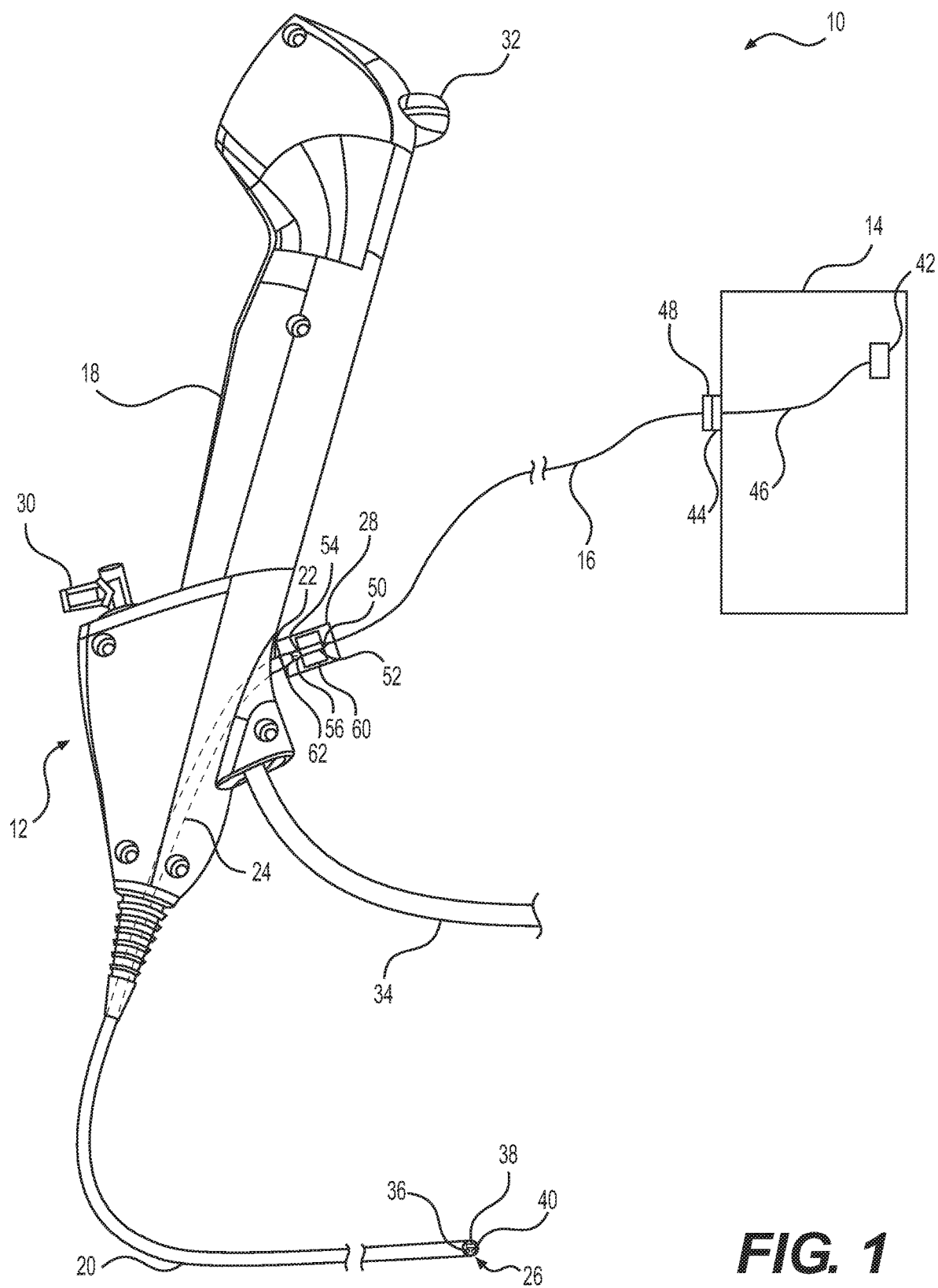
FIG. 1 illustrates a medical system, according to aspects of the present disclosure.

FIG. 1 illustrates a medical system 10 that includes a medical device 12, an illumination source 14, and a fiber 16. Medical device 12 may be an insertion device, having a handle 18 and a delivery shaft 20. Medical device 12 may include an illumination port 22 and an internal illumination lumen 24 in the handle 18. Illumination lumen 24 may include an optical fiber or bundle of fibers, and may connect through a lumen in delivery shaft 20 to a distal tip 26 of medical delivery shaft 20 to illuminate a medical procedure being performed in a patient.

Illumination source 14 may be a laser illumination source, and fiber 16 may be a laser fiber or optical fiber. Fiber 16 may also include a fiber connector 28 that may be coupled to illumination port 22 to couple fiber 16 to the medical device 12 such that illumination may propagate from fiber 16 through illumination lumen 24.

Medical device 12 may be a ureteroscope (e.g., Litho-Vue™ Single-Use Digital Flexible Ureteroscope by Boston Scientific Corp.), an endoscope, a hysteroscope, a bronchoscope, a cystoscope, or any similar device. Medical device 12 may be for single-use and be disposable, or medical device 12 may be reusable. Medical device 12 may include at least one access port 30 and a deflection lever 32 on handle 18 to steer the distal tip 26. Medical device 12 may also include a communication and power conduit 34 coupled to handle 18. Delivery shaft 20 includes at least one lumen, and may include a plurality of lumens, connecting handle 18 to distal tip 26. The at least one access port 30 may connect to a proximal end of the delivery shaft 20 through a lumen (not shown) in handle 18. Delivery shaft 20 may be maneuverable, such as, for example, by movement of deflection lever 32 or by another appropriate maneuvering element. Alternatively, delivery shaft 20 may be rigid and/or may be integrally formed with handle 18.

Distal tip 26 of medical device 12 may include an illumination output 36, a camera 38, and at least one access port output 40. Illumination output 36 connects through a lumen in delivery shaft 20 to illumination lumen 24, and may include a lens or other protective element at distal tip 26. Data captured by camera 38 may be transmitted through communication and power conduit 34. Although not shown, communication and power conduit 34 may be coupled to a power source, processing software, and/or a display unit to provide image or video of the medical procedure captured by camera 38. Access port output 40 may connect through a lumen in delivery shaft 20 to access port 30. Access port 30 allows a medical professional to provide suction or irrigation or to insert an additional medical device, for example, an energy device, such as a laser device for lithotripsy, a retrieval basket, a grasping element, a cutting instrument and/or a cautery element, through handle 18 and delivery shaft 20 to deliver medical therapy to the treatment site from access port output 40. Alternatively, medical device 12 may be a rigid scope with an integral handle and delivery shaft assembly that includes a viewing lumen such that a medical professional may manually view the medical procedure.

Illumination source 14 may include a light source 42 that generates laser energy. Illumination source 14 may have a fiber coupling 44 configured to receive fiber 16. Light source 42 may be internally connected to fiber coupling 44 by a source fiber 46, which may be surrounded by a coating as discussed below with respect to fiber 16. In one example, light source 42 may be a laser diode or a plurality of laser diodes that generate a blue color laser having a wavelength of approximately 445 nm to 455 nm, with a power of approximately 0.5 to 2.0 W. Although not shown, illumination source 14 may have a control module to control a timing, a wavelength, and/or a power of the generated laser energy. The control module may control laser selection, filtering, temperature compensation, and/or Q-switching, and may include software or hardware configured to control the generated energy. Illumination source 14 may be battery powered, or may be wire-connected to an external power source. In one example, illumination source 14 may operate light source 42 with a power supply of approximately 3.0 W.

Fiber 16 may be any illumination conveying element, such as, for example, a laser or optical fiber surrounded by a cladding, jacket, coating, or other insulating or supportive layers. In one aspect, fiber 16 may be a single filament glass fiber encased in a flexible jacket, such as, for example, a polymeric jacket. Fiber 16 may be thin and lightweight. For example, fiber 16 may have a diameter of less than approximately 1 mm. Furthermore, fiber 16 may have a diameter of approximately 0.4 mm.

As mentioned, fiber 16 may include a fiber connector 28 configured to connect to illumination port 22 on the handle 18 of the medical device 12. Fiber 16 may also include the fiber source connector 48 for connecting with fiber coupling 44 on illumination source 14. Fiber connector 28 and fiber source connector 48 are positioned on opposite ends of fiber 16. In one example, fiber connector 28 may be a male connector, and illumination port 22 may be a female connector. Alternatively, fiber connector 28 may be a female connector, and illumination port 22 may be a male connector. Similarly fiber source connector 48 may be a male connector, and fiber coupling 44 may be a female connector. Alternatively, fiber source connector 48 may be a female connector, and fiber coupling 44 may be a male connector. Alternatively or additionally, any connection to fiber 16 may be a flat junction or butt-coupling of the elements to be connected, and this connection may be secured with a clip, screw and thread, or other appropriate coupling. For example, fiber source connector 38 may couple to fiber coupling 44 in order to butt-couple fiber 16 to source fiber 46. In another example, any connection to fiber 16 may include a flat junction or butt-coupling with an aligning ferrule, with the aligning ferrule holding the connected elements and/or the connectors in contact or in close proximity. Additional securing connections or connectors between the illumination source 14, fiber 16, and illumination port 22, although not shown, may also be incorporated in system 10. In one aspect, medical device 12 may be a rigid endoscope with an approximately 4 mm diameter, and fiber 16 may be approximately 0.4 mm in diameter. Furthermore, in one aspect, fiber 16 may be permanently coupled to illumination source 14, or may be directly coupled to light source 42.

As shown in FIG. 1, illumination port 22 may be positioned on handle 18 and may be configured to couple with fiber connector 28. Illumination port 22 may be positioned at any location on handle 18 with illumination lumen 24 connecting to a lumen in delivery shaft 20. Alternatively, illumination port 22 may be incorporated in a proximal portion of delivery shaft 20.

Figure 2:
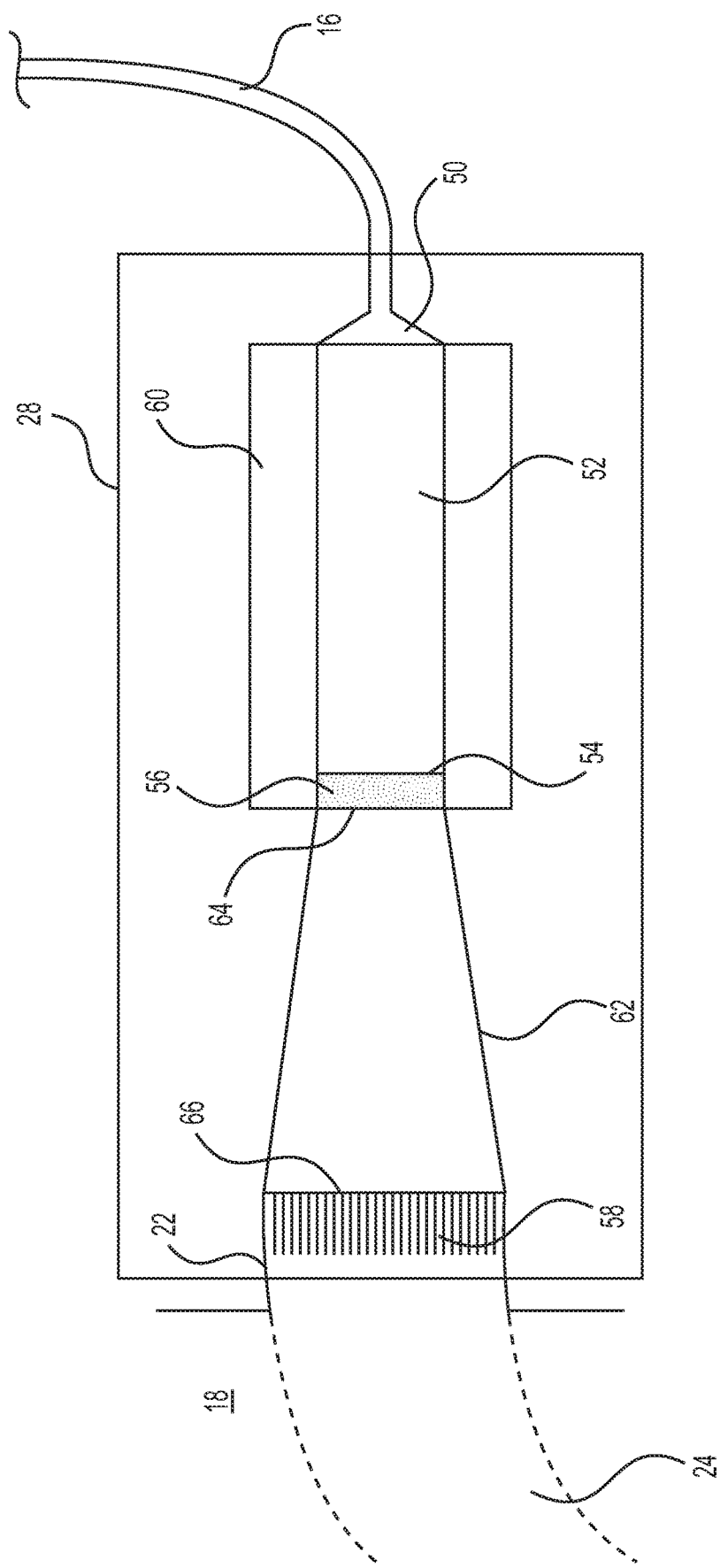
FIG. 2 illustrates a portion of the medical system of FIG. 1, according to aspects of the present disclosure.

As shown in FIGS. 1 and 2, fiber connector 28 may be an illumination converter. Fiber 16 may include an expansion portion 50 at the junction with fiber connector 28 (FIG. 2) or may be butt coupled to fiber connector 28. In one aspect, the fiber connector 28 may include a light guide 52, such as, for example, a sapphire rod. The light guide 52 may be coated on its distal surface 54 (away from coupling to fiber 16) with a fluorescent material 56, such as, for example, a polymeric material, silicone, or epoxy that includes phosphor particles. The phosphor particles may be LED phosphors, and may be high efficiency wavelength converters. LED phosphors may be similar to phosphors deposited over blue LEDs. The phosphor particles may have a low temperature sensitivity. Stated another way, the phosphor particles may be able to operate at elevated temperatures, which may result from laser pumping of the phosphor particles. Distal surface 54 may also include or be coated with non-fluorescent scattering particles, which may be mixed with the fluorescent material 56 or may be deposited at a distal end of the fluorescent material 56. The fluorescent material 56 may convert a portion, but not all, of the incident blue light (approximately 445 nm) into green light (approximately 500 nm to 600 nm) and red light (approximately 600 nm to 700 nm). Alternatively or additionally, the fluorescent material 56 may convert a portion of the incident blue light into yellow light (approximately 550 nm to 610 nm) and red light. The remaining portion of the blue light combines with the converted light to form white light 58. Therefore, the blue light is converted to white light 58 outside the cavity of the patient. Moreover, the light guide 52 may also provide a heatsink for the incident laser energy, and may also act as a light guide for the laser energy from fiber 16. Fiber connector 28 may include an outer heatsink 60, for example, an aluminum heatsink. The outer heatsink 60 may surround the light guide 52, but not surround the fluorescent material 56. Alternatively, as shown in FIG. 2, outer heatsink 60 may surround the light guide 52 and the fluorescent material 56. In one aspect, light guide 52 may include a small recess, for example, approximately 0.5 mm, at a radial center of a distal end, and the recess in light guide 52 may be filled with the fluorescent material 56.

The resulting white light 58 produced from the blue light passing through the light guide 52 and fluorescent material 56 may be emitted at all angles, and have a numerical aperture of 1, also known as "Lambertian." As such, the white light 58 may exceed the numerical aperture of the illumination port 22 and illumination lumen 24. As such, fiber connector 28 may include a numerical aperture adjustment portion, such as, for example, a numerical aperture converter 62. Numerical aperture converter 62 may be an optical element shaped like a cone or a truncated cone with an entrance face 64 and an exit face 66. Numerical aperture converter 62 may be quartz. Alternatively, numerical aperture converter 62 may be sapphire. Numerical aperture converter 62 may modify the angle of incident light. For example, as shown in FIG. 2, entrance face 64 may be smaller than exit face 66. In one aspect, the entrance face 64 may have a diameter of approximately 1.5 mm, and the exit face may have a diameter of approximately 3.0 mm or 3.5 mm. As such, the incident light, which may be "Lambertian," that enters at the entrance face 64 exits at a lower angle at the exit face 66. The white light 58 that exits numerical aperture converter 62 may then be within the acceptance angle range for the illumination lumen 24. For example, if the incident light has a numerical aperture of 1, and the numerical aperture converter 62 has an exit face diameter to entrance face diameter ratio of 2:1, the white light 58 that exits numerical aperture converter 62 may have a numerical aperture of 0.5. Light at such a numerical aperture may be accepted by illumination port 22 and illumination lumen 24, which may include a 4.0 mm illumination fiber or bundle of fibers.

Illumination lumen 24 may include an optical fiber, or may include a bundle of optical fibers. Numerical aperture converter 62 abuts illumination port 22, so the white light 58 propagates through illumination lumen 24 and delivery shaft 20 to illumination output 36. Any heat generation within illumination lumen 24 or at distal tip 26 is minimal.

Alternatively, numerical aperture converter 62 may be included in the illumination port 22. In this aspect, the fiber connector 28 includes the light guide 52, which may be coated with fluorescent material 56 on its distal surface 54. When fiber connector 28 is coupled to the handle 18 at illumination port 22, fluorescent material 56 abuts the entrance face 64 of numerical aperture converter 62. White light 58 propagates through numerical aperture 62, illumination lumen 24, and delivery shaft 20 to illumination output 36. Again, any heat generation within illumination lumen 24 or at distal tip 26 is minimal. In these aspects, the illumination emitted from illumination output 36 is clear, white light to illuminate the treatment site, allowing camera 38 to capture clear images or video for the medical procedure.

Figure 3:
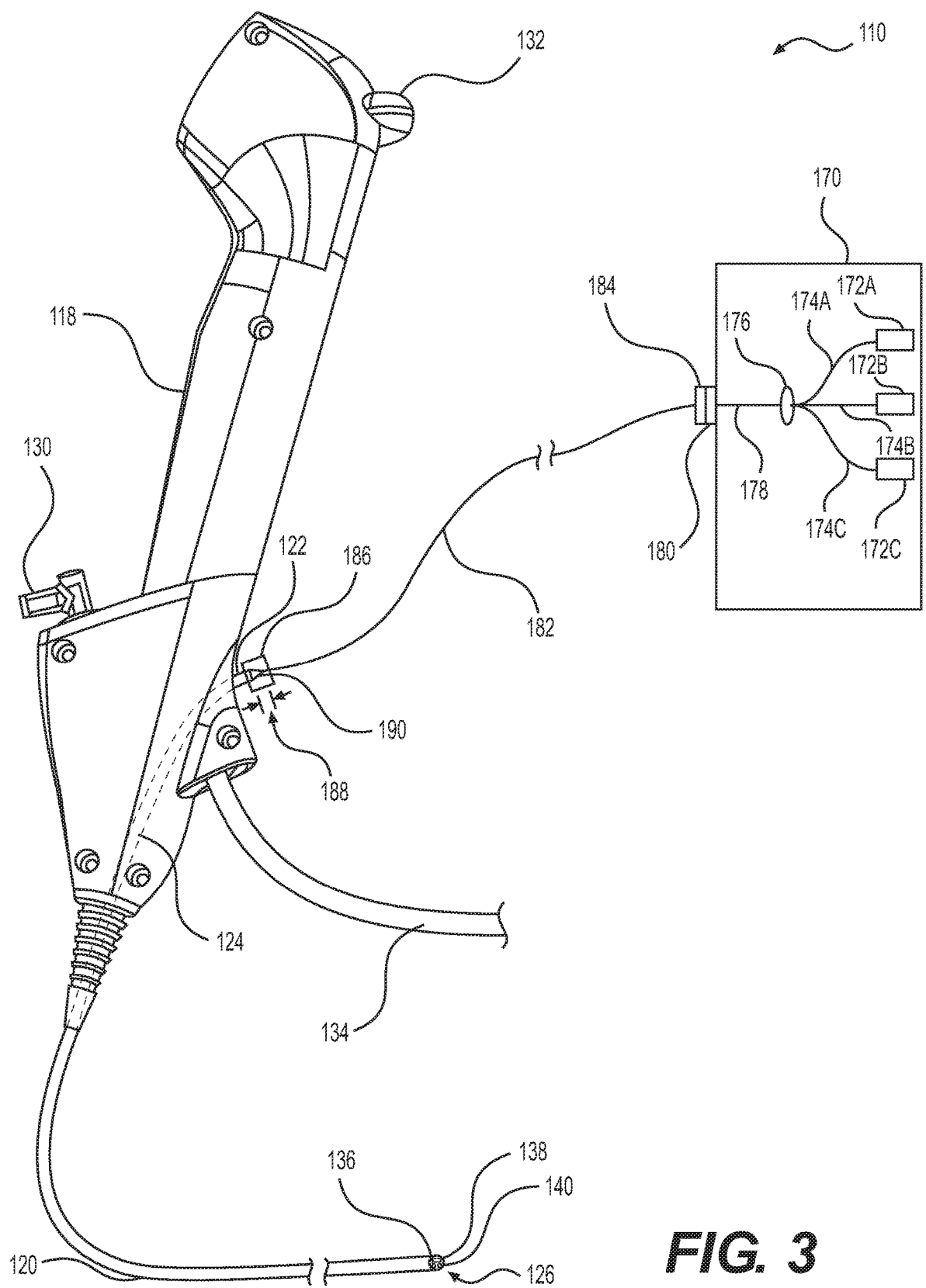
FIG. 3 illustrates a further embodiment of a medical system, according to aspects of the present disclosure.

FIG. 3 illustrates an additional embodiment of this disclosure. FIG. 3 illustrates a medical system 110 similar to medical system 10 with similar elements indicated by 100 added to the element number. Medical system 110 includes a medical device 112 comprising a handle 118 and a delivery shaft 120. Handle 118 may include an access port 130, deflection lever 132, communication and power conduit 134. Handle 118 further includes an illumination port 122 connected to a lumen in delivery shaft 120 via illumination lumen 124. Delivery shaft 120 may connect to handle 118, or may be integral with handle 118. Moreover, delivery shaft 120 may comprise a distal tip 126, which may include an illumination output 136, camera 138, and access port output 140. Alternatively, medical device 112 may be a rigid scope with an integral handle and delivery shaft assembly that includes a viewing lumen such that a medical professional may manually view the medical procedure, as discussed above.

As shown in FIG. 3, an illumination source 170 may be coupled to medical device 112 via a fiber 182. Illumination source 170 may include at least three light sources 172A, 172B, and 172C. Light sources 172A, 172B, and 172C may be different colored laser diodes. In one aspect, light source 172A may be a red laser diode configured to generate red laser energy at a wavelength of approximately 638 nm with a power of approximately 0.5 W. Light source 172B may be a green laser diode configured to generate green laser energy at a wavelength of approximately 520 nm with a power of approximately 0.25 W. Light source 172C may be a blue laser diode configured to generate blue laser energy at a wavelength of approximately 460 nm with a power of approximately 0.5 W. Light sources 172A, 172B, and 172C may generate a laser energy having a total power of 1.25 W. Illumination source 170 may include a power ratio of 1.5 Red:1.0 Green:1.5 Blue for the generated light energy, and such a power ratio may aid in the generation of white light. Furthermore, a color temperature of the generated light may be adjusted by adjusting a ratio of the red and blue light sources, keeping the green light source constant.

Each light source 172A, 172B, and 172C may be coupled to light source fibers 174A, 174B, and 174C, respectively. Light source fibers 174A, 174B, and 174C may be internal to illumination source 170, and may each be fiberoptic fibers. For example, light source fibers 174A, 174B, and 174C may be approximately 0.2 mm (200 µm) optical fibers, which may be surrounded by a jacket as discussed with respect to fiber 16 above. Light source fibers 174A, 174B, and 174C may be combined at an internal source connection 176. Internal source connection 176 may be a light guide connecting each of light source fibers 174A, 174B, and 174C to a common source fiber 178. Light source fibers 174A, 174B, and 174C may individually be coupled to common source fiber 178. Common source fiber 178 may then connect to a fiber coupling 180 to couple the illumination source 170 to fiber 182. Fiber coupling 180 may butt couple common source fiber 178 to fiber 182 via a fiber source connector 184. Alternatively, any connector assembly is also contemplated for the connection of the fiber coupling 180 to fiber source connector 184.

Alternatively, light source fibers 174A, 174B, and 174C may combine to form a three fiber cable at fiber coupling 180 where fiber 182 is coupled to illumination source 170. For example, if each light source fiber 174A, 174B, and 174C are approximately 0.2 mm in diameter, they may be combined to form a three fiber cable of approximately 0.5 mm. Fiber coupling 180 may be a butt coupling of the three fiber cable to fiber 182. Alternatively, any connector assembly is also contemplated for the connection of the fiber coupling 180 to fiber 182. Additionally, heatsinks may be incorporated at the connections with and within illumination source 170.

Once the laser energy from light source fibers 174A, 174B, and 174C enters fiber 182, or the common source fiber 178 and fiber 182, the laser energy from light sources 172A, 172B, and 172C combines to form a mixture of the laser energy. For example, if the light sources 172A, 172B, and 172C generate red, green, and blue laser energy, the combined laser energy may be white light energy transmitted through fiber 182, illumination lumen 124, and out of illumination output 136 at distal tip 126.

As mentioned above, although not shown, illumination source 170 may have a control module to control a timing, a wavelength, and/or a power of the generated laser energy from each light source 172A, 172B, and 172C. The control module may control laser selection, filtering, and/or temperature compensation, and may include software or hardware configured to control the generated energy. The control module may allow a user to adjust the wavelength or intensity of each light source 172A, 172B, and 172C. As such, the user may adjust the resulting color and intensity of the combined laser energy transmitted through fiber 182, illumination lumen 124, and out of illumination output 136 at distal tip 126. For example, a user may adjust the color temperature of the resulting combined laser energy by adjusting a power ratio of red and blue light sources, while maintaining a constant green light source. Illumination source 170 may also be battery powered, or may be wire-connected to an external power source. In one example, illumination source 170 may operate with a power supply of approximately 10 W to power light sources 172A, 172B, and 172C.

Similar to fiber 16, fiber 182 may be any illumination conveying element, such as, for example, a laser or optical fiber surrounded by a cladding, jacket, coating, or other insulating or supportive layers. In one aspect, fiber 182 may be a single filament glass fiber encased in a flexible jacket, such as, for example, a polymeric jacket. Fiber 182 may be thin and lightweight. For example, fiber 182 may have a diameter of less than approximately 1 mm. Furthermore, fiber 182 may have a diameter of approximately 0.6 mm. Fiber 182 includes a fiber connector 186. Fiber connector 186 is positioned on an opposite end of fiber 182 from fiber source connector 184.

Fiber connector 186 connects fiber 182 to illumination port 122 on the handle 118 of the medical device 112. The laser energy emitted from fiber 182 at fiber connector 186 is a complete mixture or overlap of the light energy from light sources 172A, 172B, and 172C. In one aspect, the complete mixture or overlap forms white light. This white light may be emitted at a low angle, and not be "Lambertian." Since the fiber 182 emits white light, fiber connector 186 may not include a light guide or fluorescent material. Moreover, because the fiber 182 emits white light at a low angle that can be accepted by illumination port 122 and illumination lumen 124, a heatsink is not required in fiber connector 186.

Fiber connector 186 may connect fiber 182 to illumination port 122 such that there is a numerical aperture adjustment portion, such as, for example, a coupling gap 188 between the end of fiber 182 and illumination port 122. Coupling gap 188 may allow the white light to expand in a beam expansion region 190. The coupling gap 188 may allow the white light to at least partially match an illumination aperture size of illumination port 122. In one aspect, coupling gap 188 may allow the white light to expand approximately 0.2 numerical apertures in the beam expansion region 190. In one aspect, a 7.0 mm coupling gap 188 may allow the white light emitted from the 0.6 mm diameter fiber 182 to expand before being accepted by the 4.0 mm diameter illumination port 122 and illumination lumen 124. For example, fiber connector 186 may be configured to have a screw/thread connection to illumination port 122, and the screw/thread connection may be configured such that when fully screwed in, there is a gap between the end of fiber 182 and illumination port 122 to form coupling gap 188 and beam expansion area 190. Alternatively, other mechanical arrangements of fiber connector 186 and illumination port 122 may form coupling gap 188 and beam expansion area 190. The white light may then propagate through illumination lumen 124 to illumination output 136 in distal tip 126 to illuminate the treatment site. In one aspect, the white light propagated from illumination output 136 may be approximately 100 lumens.

Fiber connector 186 may connect to illumination port 122 in any configuration discussed above, or fiber 186 may terminate at fiber connector 186 and form a flat junction where fiber 186 is coupled to illumination port 122. The connection of fiber connector 186 to illumination port 122 may be secured with a clip, screw and thread, or other appropriate coupling. Additional securing connections or connectors between the illumination source 170, fiber 182, and illumination port 122, although not shown, may also be incorporated in system 110.

In the systems and methods discussed above, a user may couple illumination source 14, 170 to the handle 18, 118 of a medical device 12, 112 via fiber 16, 182 and the corresponding fiber connector 28, 186. With the delivery shaft 20, 120 of medical device 12, 112 inserted into a patient, or during insertion and manipulation of the distal tip 26, 126, the user may activate illumination source 14, 170 in order to illuminate a treatment site. Because the light energy from illumination source 14, 170 is converted to white light 58 outside of the handle 18, 118 and the patient, the risks of harming the patient or the medical professional may be reduced. Because white light 58 is delivered to the treatment site, the user may more clearly visualize, either directly or via camera 38, 138 the insertion, manipulation, procedure, and body features at the treatment site. Moreover, fiber 16, 182 and the corresponding fiber connector 28, 186 are small and lightweight, so the user may maneuver and hold the handle 18, 118 throughout the procedure without the inconvenience or restrictions of a heavier or more bulky cable. Since light source(s) 42, 172A, 172B, 172C has/have minimal power requirements and may be battery powered, illumination source 14, 170 may provide added maneuverability, reduced equipment footprint, reduced cost, and lower power consumption.

While principles of the present disclosure are described herein with reference to illustrative examples for particular applications, it should be understood that the disclosure is not limited thereto. Those having ordinary skill in the art and access to the teachings provided herein will recognize additional modifications, applications, embodiments, and substitution of equivalents all fall within the scope of the features described herein. Accordingly, the claimed features are not to be considered as limited by the foregoing description.

We claim:

1. An illumination device comprising:
    an illumination source including a light source;
    a single fiber configured to connect the illumination source to a medical device and being dedicated to the transmission of light energy from the light source; and
    a numerical aperture adjustment portion and a light guide between the single fiber and the medical device, wherein the light guide is between the single fiber and the numerical aperture adjustment portion,
    wherein the light source generates at least one non-white colored laser energy, and wherein the illumination device converts the at least one non-white colored laser energy into white colored laser energy.

2. The illumination device of claim 1, wherein the single fiber is a single filament glass fiber having a diameter of approximately 0.4 mm, and wherein the single fiber is encased in a flexible polymeric jacket.

3. The illumination device of claim 1, wherein the light source is battery powered.

4. The illumination device of claim 1, wherein the light source includes at least one laser diode to generate a blue color laser having a wavelength of approximately 445 to 455 nanometers.

5. The illumination device of claim 4, wherein the single fiber includes a connector configured to couple the single fiber to the medical device, wherein the connector includes the light guide and a heatsink, and wherein the numerical aperture adjustment portion is a truncated cone that includes an exit face larger than an entrance face.

6. The illumination device of claim 5, wherein the light guide includes a sapphire rod, wherein an end of the sapphire rod is coated with a fluorescent material that includes phosphor particles and non-fluorescent scattering particles in a polymeric material, and wherein the fluorescent material abuts the numerical aperture adjustment portion.

7. The illumination device of claim 1, wherein the light source includes at least one red laser diode configured to generate a red color laser, at least one green laser diode configured to generate a green color laser, and at least one blue laser diode configured to generate a blue color laser; and
    wherein the at least one red laser diode, the at least one green laser diode, and the at least one blue laser diode are each coupled to a light source fiber, and wherein the light source fibers are coupled to form one source fiber within the illumination source to form white laser energy.

8. The illumination device of claim 1, wherein the light source includes at least one red laser diode configured to generate a red color laser, at least one green laser diode configured to generate a green color laser, and at least one blue laser diode configured to generate a blue color laser; and
    wherein the at least one red laser diode, the at least one green laser diode, and the at least one blue laser diode are each coupled to a light source fiber, and wherein the light source fibers are coupled to the single fiber to form white laser energy.

9. The illumination device of claim 1, wherein the single fiber includes a connector configured to couple the single fiber to the medical device, and wherein the numerical aperture adjustment portion is a beam expansion portion between an end of the single fiber and the medical device.

10. An illumination device comprising:
an illumination source; and
an illumination conveying element,
wherein the illumination conveying element includes a connector configured to connect the illumination conveying element to a medical device, wherein the connector includes a light guide and a numerical aperture converter, wherein the light guide is between the illumination conveying element and the numerical aperture converter, wherein a surface of the light guide is coated with a fluorescent material, and wherein the fluorescent material abuts the numerical aperture converter.

11. The illumination device of claim 10, wherein the illumination source includes at least one laser diode to generate a blue color laser having a wavelength of approximately 445 to 455 nanometers.

12. The illumination device of claim 10, wherein the numerical aperture converter is a truncated quartz cone having an entrance face and an exit face, the entrance face having a smaller diameter than the exit face; and
wherein the fluorescent material is a silicone based material that includes fluorescent phosphor particles and non-fluorescent scattering particles.

13. The illumination device of claim 10, wherein the illumination conveying element is a single filament glass fiber encased in a flexible polymeric jacket; and
wherein the illumination conveying element has a diameter of approximately 0.4 mm.

14. The illumination device of claim 10, wherein when the connector is coupled to the medical device, and at least one illumination lumen within the medical device directs illumination to a distal end of the medical device.

15. An illumination device comprising:
an illumination source;
a fiber; and
a fiber connector connecting the fiber to an illumination port in a medical device, wherein the fiber connector includes a coupling gap between an end of the fiber and the illumination port,
wherein the illumination source includes at least three light energy sources, each having a different wavelength, and
wherein light energy from the light energy sources combines to form white light either within the fiber or before being transmitted into the fiber.

16. The illumination device of claim 15, wherein the laser energy sources include at least one red laser diode configured to generate a red color laser, at least one green laser diode configured to generate a green color laser, and at least one blue laser diode configured to generate a blue color laser.

17. The illumination device of claim 16, wherein the at least one red laser diode, the at least one green laser diode, and the at least one blue laser diode are each coupled to a light source fiber, and wherein the light source fibers are coupled to form one source fiber within the illumination source to form white laser energy.

18. The illumination device of claim 16, wherein the at least one red laser diode, the at least one green laser diode, and the at least one blue laser diode are each coupled to a light source fiber, and wherein the light source fibers are coupled to the fiber to form white laser energy.

19. The illumination device of claim 15, wherein the coupling gap allows light energy from the fiber to expand approximately 0.2 numerical apertures.

20. The illumination device of claim 15, wherein the fiber connector includes a light guide and a numerical aperture converter, wherein the light guide is between the illumination conveying element and the numerical aperture converter, wherein a surface of the light guide is coated with a fluorescent material, and wherein the fluorescent material abuts the numerical aperture converter.

\* \* \* \* \*